United States Patent
Morrison

(10) Patent No.: US 8,333,774 B2
(45) Date of Patent: Dec. 18, 2012

(54) SUTURING INSTRUMENT WITH NEEDLE DOCK

(75) Inventor: David S. Morrison, Long Beach, CA (US)

(73) Assignee: Arthrex, Inc., Naples, FL (US)

( * ) Notice: Subject to any disclaimer, the term of this patent is extended or adjusted under 35 U.S.C. 154(b) by 1415 days.

(21) Appl. No.: 10/969,175

(22) Filed: Oct. 21, 2004

(65) Prior Publication Data

US 2005/0090841 A1 Apr. 28, 2005

Related U.S. Application Data

(60) Provisional application No. 60/513,209, filed on Oct. 23, 2003.

(51) Int. Cl.
*A61B 17/04* (2006.01)

(52) U.S. Cl. ........................................ 606/139; 606/148

(58) Field of Classification Search .................. 606/139, 606/144–148, 222–232, 184, 185; 600/585; 604/532

See application file for complete search history.

(56) References Cited

U.S. PATENT DOCUMENTS

| | | | | |
|---|---|---|---|---|
| 4,641,652 A * | 2/1987 | Hutterer et al. | ................ | 606/148 |
| 4,683,885 A * | 8/1987 | Hutterer et al. | .................. | 606/1 |
| 5,318,578 A * | 6/1994 | Hasson | .......................... | 606/139 |
| 5,322,509 A * | 6/1994 | Rickerd | ......................... | 604/532 |
| 5,348,545 A * | 9/1994 | Shani et al. | ..................... | 604/532 |
| 5,368,595 A * | 11/1994 | Lewis | ............................... | 606/72 |
| 5,562,685 A * | 10/1996 | Mollenauer et al. | .......... | 606/144 |
| 5,665,096 A * | 9/1997 | Yoon | .............................. | 606/139 |
| 5,755,728 A * | 5/1998 | Maki | ............................. | 606/145 |
| 5,830,220 A | 11/1998 | Wan et al. | | |
| 5,908,426 A * | 6/1999 | Pierce | ........................... | 606/139 |
| 6,511,487 B1 | 1/2003 | Oren et al. | | |
| 6,517,578 B2 * | 2/2003 | Hein | .......................... | 623/13.13 |
| 6,626,917 B1 * | 9/2003 | Craig | ............................ | 606/144 |
| 6,786,913 B1 | 9/2004 | Sancoff et al. | | |
| 7,108,700 B2 * | 9/2006 | Chan | ............................. | 606/139 |

* cited by examiner

*Primary Examiner* — Kathleen Sonnett
(74) *Attorney, Agent, or Firm* — Dickstein Shapiro LLP

(57) ABSTRACT

A suturing instrument having a dock at the end for receiving and securing a needle attached to a suture. The suturing instrument includes a cannulated handle attached to the proximal end of a cannulated shaft. The proximal end of a needle is removably received and securely received in the curved needle dock formed on the distal end of the shaft. The suture attached to the needle passes through the shaft and out the proximal end of the handle. Once the instrument is inserted into the body (usually through a cannula), the suture is retracted at the proximal end of the instrument handle, which draws the attached needle into the needle dock. The suture dock preferably has a compound curvature which prevents substantial rotation of the needle upon insertion.

8 Claims, 2 Drawing Sheets

SUTURING INSTRUMENT WITH NEEDLE DOCK

This application claims the benefit of U.S. Provisional Application No. 60/513,209, filed Oct. 23, 2003, the entire disclosure of which is incorporated by reference herein.

FIELD OF THE INVENTION

The present invention relates to surgical suturing instruments and, in particular, to a suturing instrument with a dock for capturing and securing a needle attached to suture.

BACKGROUND OF THE INVENTION

Many surgical suturing instruments have been developed to assist surgeons in threading suture through tissue. A typical suturing instrument currently used for suturing during endoscopic surgery includes at one end movable jaws for grasping and releasing a needle, and at the opposite end a scissor-like control handle, which is used to open and close the jaws and to move the needle. The surgeon grasps the needle by closing the jaws around it, and then inserts the needle into and through the tissue and opens the jaws to release the needle. Next, the surgeon uses the same instrument or similar tool to grasp the needle and pull it through the tissue. The movements are repeated, as necessary, to complete the suturing procedure.

During suturing, the surgeon has to release and re-grasp the needle a number of times. Each time the surgeon re-grasps the needle, the needle must be positioned and oriented correctly within the jaws, so that it is readily inserted into and through the tissue to make another stitch. Accordingly, the surgeon must first determine the position and orientation of the needle in the jaws. This operation is difficult, particularly in endoscopic procedures, because the view of the needle and of the instrument is via a two-dimensional image transmitted by a camera to the surgeon. Next, the surgeon must adjust the needle within the jaws, as necessary, which is also difficult because the jaws only open and close. Further, the surgeon must ensure that the needle is not dropped, since the needle may be difficult to locate in the transmitted image. Once a dropped needle is located, picking it up is difficult, particularly with the suturing instrument. Often, a special instrument and another hand to manipulate the instrument are required.

Accordingly, it would be desirable to provide a suturing instrument that can be accurately positioned and oriented relative to the tissue to be sutured, and that can be further manipulated in an efficient, consistent and precise manner even in very tight surroundings such as arthroscopic or laproscopic surgery. A suturing instrument which eliminates the need for mechanical jaws, and which is easy to employ in minimally invasive procedures or other procedures in which the direction of the access to the tissue to be sutured is limited, is also desirable.

SUMMARY OF THE INVENTION

The present invention provides a suturing instrument including a cannulated handle attached to the proximal end of a cannulated shaft. The proximal end of a needle attached to a length of suture can be received and securely held in a needle dock formed on the distal end of the shaft. The suture attached to the needle passes through the shaft and out the proximal end of the handle. Pulling on the suture proximally draws the needle into the needle dock. The needle can be secured in a docked position by wedging the suture into a V-shaped notch formed proximally on the handle.

The suturing instrument of the present invention can be used in arthroscopic or mini-open procedures, for example. The needle is held in the docked position by securing the suture in the notch on the proximal end of the instrument handle. The surgeon uses the instrument to pierce through tissue to be repaired with the needle. Once the needle is advanced through the tissue, the proximal end of the suture is released from the notch. Drawing the handle away from the tissue causes the needle to separate from the dock, with the suture attached to the needle for further suturing steps.

These and other features and advantages of the invention will become apparent from the following detailed description that is provided in connection with the accompanying drawings and illustrated exemplary embodiments of the invention.

DETAILED DESCRIPTION OF THE PREFERRED EMBODIMENTS

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The term "endoscopy" encompasses arthroscopy, laparoscopy, hysteroscopy, among others, and endoscopic surgery involves the performance of surgical procedures within a patient's body through small openings as opposed to conventional open surgery through large incisions.

Figure 1:
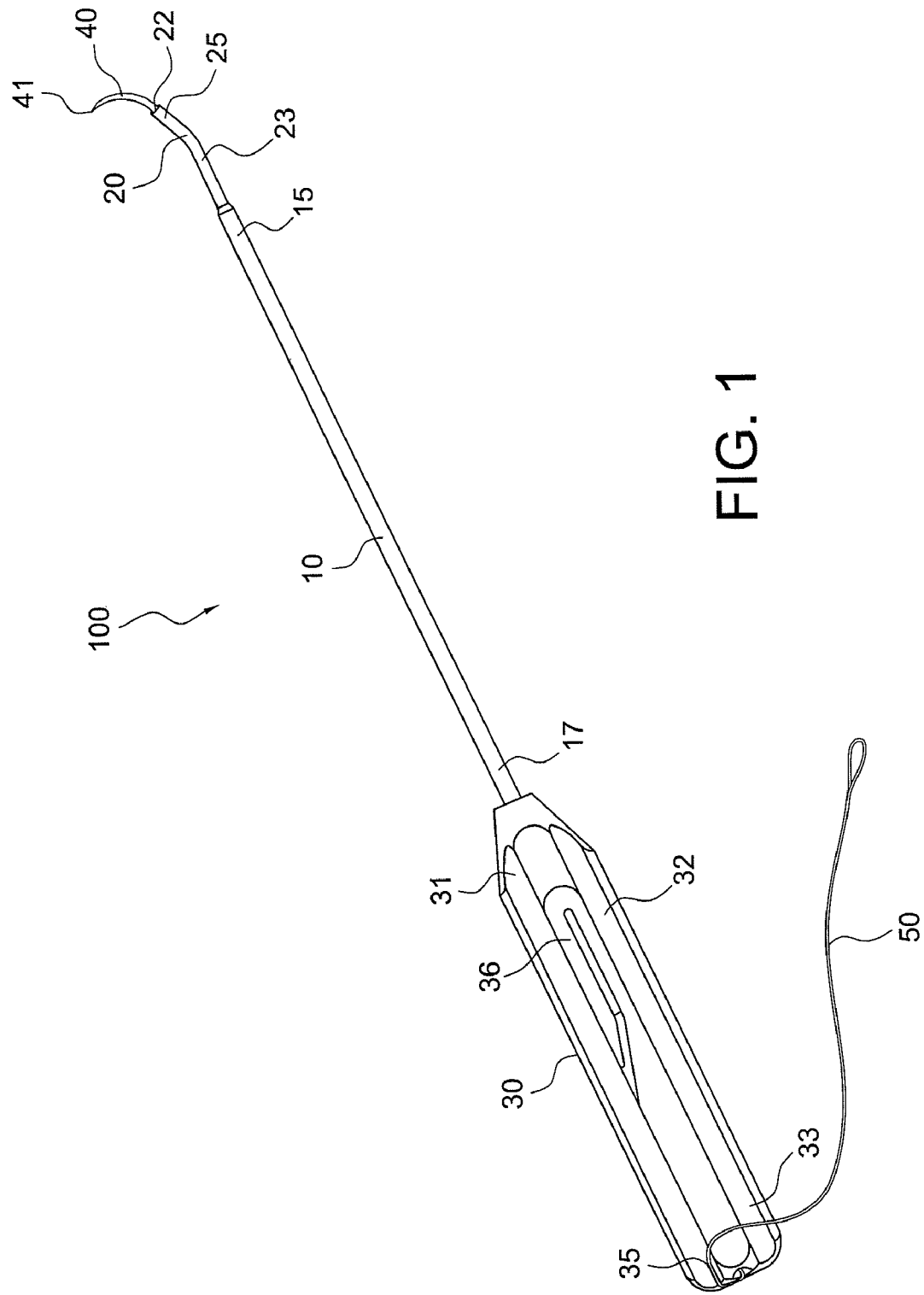
FIG. 1 is a plan view of a suturing instrument according to the present invention with the needle in the docked position.
Figure 2:
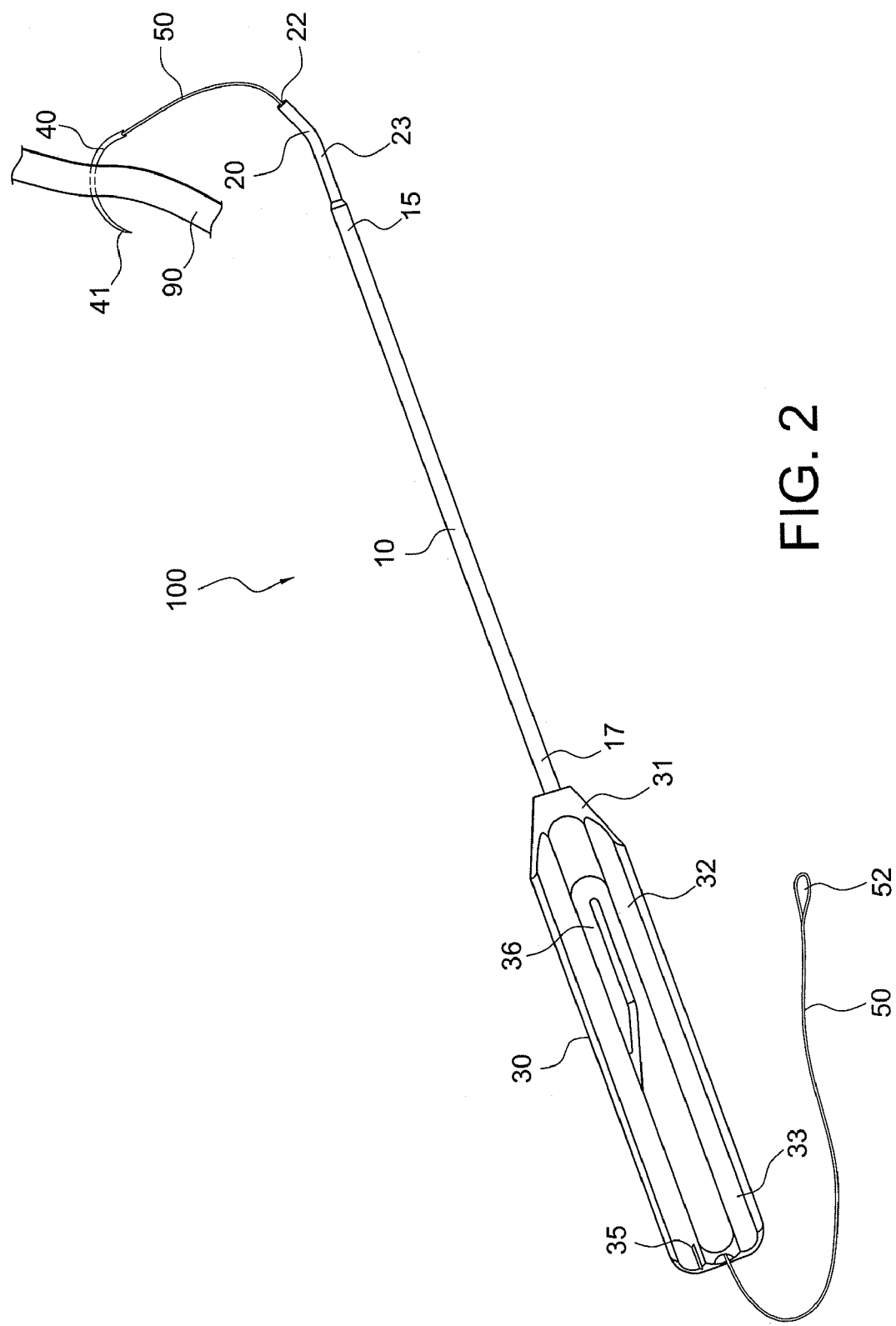
FIG. 2 is a plan view of a suturing instrument according to the present invention with the needle released from the dock and shown schematically piercing a section of tissue to be repaired.

Referring now to the drawings, where like elements are designated by like reference numerals, FIGS. 1 and 2 illustrate a surgical instrument 100 of the present invention for suturing anatomical tissue within a patient. As detailed below, the surgical suturing instrument includes a handle and a shaft that is provided at its distal end with a needle dock having a curved and/or coiled configuration that securely engages a needle attached to a length of suture. The surgical suturing instrument 100 of FIGS. 1 and 2 may be employed, for example, in a wide variety of suturing applications including closing ruptured or incized tissues, soft tissue attachment, anastamosis, attachment of grafts and mesh, among many others. In particular, the curved surgical instrument allows it to be introduced into small openings for endoscopic procedures wherein access to the tissue to be sutured is difficult and wherein the position and orientation of the needle and attached suture cannot be easily assessed by the surgeon.

The suturing instrument 100 preferably comprises an elongate, narrow diameter body or shaft assembly 10 suitable for use in remote procedures performed through percutaneous tissue punctures, such as vascular closures, arthroscopic, laparoscopic and other invasive procedures and the like. The shaft assembly has a length of about 5 cm to about 20 cm, preferably about 15 cm. The diameter of the shaft assembly is sufficiently small to facilitate introduction through access sheaths, cannulas, trocars, and the like, typically being less than about 10 mm, preferably about 5 to about 7 mm.

As illustrated in FIGS. 1 and 2, the shaft assembly 10 is elongated and cannulated to allow a suture strand to freely pass through the shaft assembly, as described below. The shaft assembly 10 is provided with a substantially straight or linear region 15, which is adjacent to a substantially curved region 20. As described below, the curved region 20 has a compound curve (i.e., it curves in more than one dimension) and is employed as a needle dock (or needle docking region) for engaging and securing a needle 40 attached to a strand of suture 50. Although the embodiments of the present invention will be described below with reference to a suturing instrument having a curved needle dock region, preferably a compound curved region or "corkscrew" configuration, the invention also contemplates a suturing instrument having a needle dock region that has a configuration which is not necessarily curved, but rather designed in accordance with the geometry of the needle to be secured.

The substantially curved region 20 of instrument 100 has a proximal end 23 and a distal end 25 and a diameter smaller than that of the substantially linear region 15. The proximal end 17 of the shaft has the handle assembly designed to facilitate manual manipulation of the device and to manipulate the suture attached to the needle to allow the needle to dock and undock from the needle docking region 20.

As illustrated in FIGS. 1 and 2, the distal end 25 of the needle docking region 20 is provided with an opening 22 that allows the needle 40 (with attached suture strand 50) to be securely positioned and oriented within the distal end 25 of the needle docking region 20. Opening 22 is dimensioned to have an inner diameter about equal to the outer diameter of the needle 40, to allow the needle 40 to be securely held within the docking region 20. Advantageously, the compound curvature of region 20 prevents the needle 40 from rotating substantially after insertion, allowing the surgeon to easily pronate and manipulate the mounted needle through tissue. The edges of opening 22 are preferably beveled so that they do not abrade the suture as it is pulled through the instrument.

The shaft or body assembly 10 of the suturing instrument 100 may have a round or oval cross-sectional shape. The needle docking region 20 of the shaft or body assembly 10 is formed of a rigid, medically acceptable metal or plastic material, preferably stainless steel. The linear region 15 of the body assembly 10 may be also formed of stainless steel or diamond knurl, and is surrounded by the handle assembly 30. Preferably, the needle docking region 20 has a length of about 0.5 cm to about 3 cm, preferably about 1 cm. As shown in FIGS. 1 and 2, the needle docking region 20 is substantially curved, in that about 60 to 100%, more preferably of about 80 to 100%, of its length is curved relative to the longitudinal axis of the handle assembly 30.

A handle assembly 30 is provided at proximal end 17 of the substantially straight or linear region 15. The handle assembly 30 has a proximal end 33 and a distal end 31. The handle assembly 30 is also cannulated to allow the suture strand 50 to freely pass through it and out the proximal end 33 of handle 30. The outer diameter of the shaft assembly 10 is smaller than the inner diameter of the handle 30 and is securely fixed within the handle 30. The handle 30 is provided with a plurality of protuberances 32 of various configurations and sizes, to allow easy manipulation by a surgeon.

An indentation or notch 35, preferably a V-shaped notch, is provided at the proximal end 33 of the handle assembly 30. As described below, the V-shaped notch allows the suture strand 50 that exits the proximal end 33 of the handle to be received and secured within the notch during suturing. A suture cleat 36 is provided adjacent the V-shaped notch 35 and allows the suture strand to wrap around the suture cleat 36 and to be additionally secured. Preferably, the suture cleat 36 has a raised configuration relative to the protuberances 32 of the handle 30, to allow a user to easily identify the suture cleat and, accordingly, the position of the V-shaped notch 35.

Providing the suture cleat 36 in close proximity to the V-shaped notch 35 allows a user to easily maneuver the suture prior to the suturing procedure and to optionally secure it around the suture cleat. Additionally, once the suture strand is secured within the V-shaped notch 35 and optionally wrapped around the suture cleat 36, the user can easily assess the position of tip 41 of the docked needle relative to the tissue to be pierced and sutured, especially in procedures where the user's visibility is reduced.

As shown in FIG. 1, in the "docked" position, needle 40 is secured within the distal end 22 of the needle docking region 20 so that it does not rotate relative to its axis during surgery. Thus, in the "docked" position, needle 40 is docked within the distal end 22 of the needle docking region 20 and also locked within the distal end 22 so it cannot move and/or rotate in any direction. Conversely, in the "undocked" position, needle 40 is not docked within the distal end 22 of the needle docking region 20, but rather rests along the side of the needle docking region 20 being able to freely rotate and move in any direction.

Needle 40 may be curved or hooked. Preferably, in the "docked" position, about half the curved length of the needle 40 is housed within the corresponding curved distal end 22 of the needle docking region 20, to assist in surgically manipulating the docked needle. Needle 40 is held in place at the distal end 22 of the instrument 100 by wedging flexible strand of suture 50 into the V-shaped notch 35 formed at the proximal end 33 of the handle 30. The needle 40 may be secured to the suture 50 by crimping, for example, although many other methods of securing the needle to the suture could be used.

During surgery, the surgical instrument 100 with the needle 40 in the undocked position is introduced through a cannula and passed into a surgical site so that the needle 40 is brought into the proximity of tissue 90 (FIG. 2) to be repaired. As the needle 40 is maintained in the undocked position, the advance of the instrument 100 through the cannula, with the needle aside the shaft of the instrument, is easily facilitated. Once the undocked needle 40 is passed through the cannula, needle 40 is secured in the docked position, as shown in FIG. 1, by pulling proximally the suture strand 50 and securing the suture strand 50 within the V-shaped notch 35 and optionally around the suture cleat 36 of the handle 30. By pulling proximally the suture strand 50 and securing the suture around the V-shaped notch 35, the needle 40 is tightly secured within the needle docking region 20 so that it cannot rotate within the needle docking region 20 and relative to its axis.

With the needle 40 secured in the docked position, the handle 30 of instrument 100 is manipulated such that tip 41 of the docked needle 40 pierces through tissue 90. The needle is undocked by releasing the suture 50 from the V-shaped notch 35 on handle 30, and drawing back on the instrument handle. As the instrument handle 30 and shaft 10 are withdrawn from the surgical site, needle 40 separates from the needle docking region 20, with the suture 50 remaining in place and attached to needle 40, ready for subsequent suturing steps. For example, end loop 52 of the suture 50 may be employed to shuttle a limb of another strand of suture (which, for example, may be attached to a suture anchor) and to introduce it though a lateral cannula to facilitate tying of that suture limb.

The surgical instrument 100 of the present invention described above with reference to FIGS. 1 and 2 may be employed for suturing during various surgical medical procedures. For example, the suturing instrument 100 may be employed in endoscopic and arthroscopic procedures, including but not limited to arthroscopic rotator cuff repair, meniscal repair, and any orthopaedic procedure that requires manipulation of suture through soft tissue, for example. Additionally, the instrument 100 may be utilized in other general surgical and specialty procedures that require suturing at a remote site, such as inside the body. The instrument of the present invention may be also used in repairs where suture visibility or finger access can be limited.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed is:

1. A method of suturing tissue, the method comprising the steps of:
    providing a suturing instrument comprising a cannulated shaft having a curved distal end and a cannulated handle coupled to the cannulated shaft, the cannulated handle being provided with a notch located at a proximal end of the handle, the curved distal end being provided with a distal opening having an inner diameter;
    inserting the shaft of the instrument through a cannula so that the distal end is in proximity of tissue to be sutured;
    docking a proximal end of a needle for piercing through tissue within the curved distal end of the instrument, the needle having an outer diameter which is about equal to the inner diameter of the distal opening of the curved distal end to allow about half of the length of the needle to be securely held within the distal opening of the curved distal end, the distal curved end having a compound curvature to prevent rotation of the needle upon insertion, the needle being attached to a suture strand passing through the cannulated shaft, through the curved distal end and through the handle, the suture strand terminating in a loop at an end of the suture strand opposite to the needle;
    pulling proximally on the suture strand extending outside the handle to dock the needle on the instrument;
    piercing anatomical tissue with the needle; and
    shuttling a limb of another suture strand with the loop and tying the limb.

2. The method of claim 1, further comprising the step of securing a proximal region of the needle within the curved distal end of the instrument by securing the strand of suture in the notch on the handle.

3. The method of claim 2, wherein the notch is a V-shaped notch.

4. The method of claim 2, further comprising the step of releasing the strand of suture from the notch on the handle, to allow the needle to be released from the curved distal end of the instrument.

5. A method of suturing anatomical tissue using a length of suture attached to a needle, the method comprising the steps of:
    providing a suturing instrument comprising a cannulated shaft having a curved distal end and a linear proximal end, a cannulated handle coupled to the cannulated shaft, and a curved needle for piercing through tissue, the needle being attached to a suture strand, the suture strand passing through the cannulated shaft and handle, the suture strand terminating in a loop at an end of the suture strand opposite to the needle, wherein the curved distal end is provided with a distal opening with an inner diameter about equal to an outer diameter of the curved needle, to allow about half of the length of the curved needle to be securely held within the curved distal end, the distal curved end having a compound curvature to prevent rotation of the needle upon insertion;
    inserting the shaft of the instrument through a cannula so that the distal end of the shaft is in proximity of tissue to be sutured;
    pulling proximally the suture strand to draw a proximal end of the curved needle into secure engagement with the curved distal end of the instrument shaft, the curvature of the shaft preventing substantial rotation of the needle;
    manipulating the suturing instrument with the secured curved needle to cause the curved needle to pierce the anatomical tissue to be sutured;
    shuttling another suture strand with the loop of the suture strand, the another suture strand being attached to an anchor; and
    introducing the another suture strand with the anchor through another cannula.

6. The method of claim 5, further comprising the step of securing the strand of suture into a notch in the handle subsequent to the step of pulling proximally the suture strand.

7. The method of claim 6, further comprising the step of releasing the strand of suture from the notch of the handle to allow the curved needle to be released from the curved distal end of the shaft.

8. The method of claim 7, further comprising the step of pulling the released needle through the anatomical tissue to be sutured.

* * * * *